United States Patent [19]

Obayashi et al.

[11] 3,951,603

[45] Apr. 20, 1976

[54] GAS-SENSOR ELEMENT AND METHOD FOR DETECTING REDUCING GAS OR OXYGEN GAS

[75] Inventors: Hidehito Obayashi; Tetsuo Gejyo, both of Tokyo, Japan

[73] Assignee: Hitachi, Ltd., Japan

[22] Filed: July 5, 1973

[21] Appl. No.: 376,276

[30] Foreign Application Priority Data

July 8, 1972 Japan.............................. 47-68308
Nov. 15, 1972 Japan.............................. 47-113867
May 4, 1973 Japan.............................. 48-49094

[52] U.S. Cl. .............................. 23/232 E; 338/34; 23/254 E; 73/27 R
[51] Int. Cl.² .................. G01N 27/04; H01C 13/00
[58] Field of Search ................. 23/232 E, 254 E; 73/27 R; 338/34; 324/71 SN

[56] References Cited
UNITED STATES PATENTS

| | | | |
|---|---|---|---|
| 3,609,732 | 9/1971 | Kasahara et al................... | 23/254 E |
| 3,625,756 | 12/1971 | Taguchi.......................... | 23/254 E X |
| 3,644,147 | 2/1972 | Young............................ | 252/461 UX |
| 3,695,848 | 10/1972 | Taguchi.......................... | 23/254 E |
| 3,732,519 | 5/1973 | Taguchi.......................... | 338/34 |
| 3,793,605 | 2/1974 | Fehlner.......................... | 338/34 |

FOREIGN PATENTS OR APPLICATIONS

| | | | |
|---|---|---|---|
| 1,352,995 | 5/1974 | United Kingdom.......... | 252/461 UX |
| 2,119,702 | 11/1971 | Germany..................... | 252/461 UX |

OTHER PUBLICATIONS

Galasso, *Structure Properties and Preparation of Perovskite-Type Compounds,* Pergamon Press, N.Y. (1970), pp. 60–73.

*Primary Examiner*—Morris O. Wolk
*Assistant Examiner*—Timothy W. Hagan
*Attorney, Agent, or Firm*—Craig & Antonelli

[57] ABSTRACT

A gas-sensor element for detecting reducing gases and vapors such as alcohols or carbon monoxide, or for determining oxygen concentration, which is characterized by comprising a complex metal oxide having a perovskite-type crystal structure and represented by the general formula $A_{1-x}A'_xBO_{3-\delta}$, wherein A is at least one element selected from the group consisting of rare earth elements of the atomic numbers from 57 to 71, yttrium, and hafnium, A' is at least one element selected from the group consisting of alkaline earth metals and lithium, B is at least one element selected from the group consisting of transition metals of the atomic numbers from 21 to 30, O is oxygen, $x$ is in the range of $0 \leq x \leq 1$, and $\delta$ is a nonstoichiometric parameter.

36 Claims, 18 Drawing Figures

GAS-SENSOR ELEMENT AND METHOD FOR DETECTING REDUCING GAS OR OXYGEN GAS

BACKGROUND OF THE INVENTION

This invention relates to a sensor element for detecting trace amounts of gaseous reducing substances such as alcohols, aldehydes, hydrocarbons, carboxylic acids, amines, and carbon monoxide contained in the atmosphere, exhaust gases, the breath, etc., or for determination of oxygen concentration and a method for detecting the gaseous substances.

For detecting trace amounts of reducing gases contained in these atmospheres, there have been conventionally known such methods as gas chromatography and a method of detection by use of a semi-conductor element. As for the gas chromatography, it cannot be said to be a convenient and inexpensive detecting method because it requires a large-scale apparatus and a certain degree of skill for analytical procedures. Among detecting methods which make use of a semiconductor element as the sensor, there has been known, for example, a method which utilizes the change in specific resistance of a shaped piece comprising n-type stannic oxide as the main constituent, resistance change of which takes place by adsorption of ethanol vapor. This method, however, has such disadvantages that the ethanol vapor once adsorbed on the sensor will not be desorbed unless the sensor is heat-treated at a temperature of 350° C. or higher, and, in addition, the sensor has an extremely large temperature coefficient of resistance, viz. about 5 to 10%/° C.

On the other hand, for detecting oxygen concentration in the atmosphere, there is known a method in which a galvanic cell is employed. This method, however, has such disadvantages that the response is slow, the life of the element is only about 6 months counting from preparation of the element, and the solution contained in the sensing element will raise a problem of maintenance.

There is known also another method for measuring oxygen concentration by the solid-state oxygen concentration cell method which employs an oxygen ion conductive solid electrolyte such as, for example, $(Zr, Ca)O_{2-y}$. According to this method, the partial pressure of oxygen in a sample gas is measured by the oxygen concentration cell method using gaseous oxygen, in which the oxygen partial pressure $P_{O_2}$ is 1.0 atm, or air, in which the oxygen partial pressure is 0.21 atm, as the standard gas for reference. This method, however, has such disadvantages that the sensor will not operate with stability unless the temperature is above about 800° C., and the output voltage is low in case oxygen concentration of the sample gas approximates that of the standard gas.

SUMMARY OF THE INVENTION

This invention relates to a gas-sensor element which may detect rapidly and quantitatively a reducing gas contained in the atmosphere, exhaust gases, or the breath, or an oxygen concentration, and which has stable response performance. More particularly, this invention relates to a gas-sensor element characterized by comprising a complex metal oxide having a perovskite-type crystal structure and represented by the general formula $A_{1-x}A'_xBO_{3-\delta}$, wherein A is at least one element selected from the group consisting of rare earth elements of the atomic numbers from 57 to 71, yttrium, and hafnium, A' is at least one element selected from the group consisting of alkaline earth metals and lithium, B is at least one element selected from the group consisting of transition metals of the atomic numbers from 21 to 30, O is oxygen, $x$ is in the range of $0 \leq x \leq 1$, and $\delta$ is a nonstoichiometric parameter.

DESCRIPTION OF THE PREFERRED EMBODIMENTS

Figure 1:
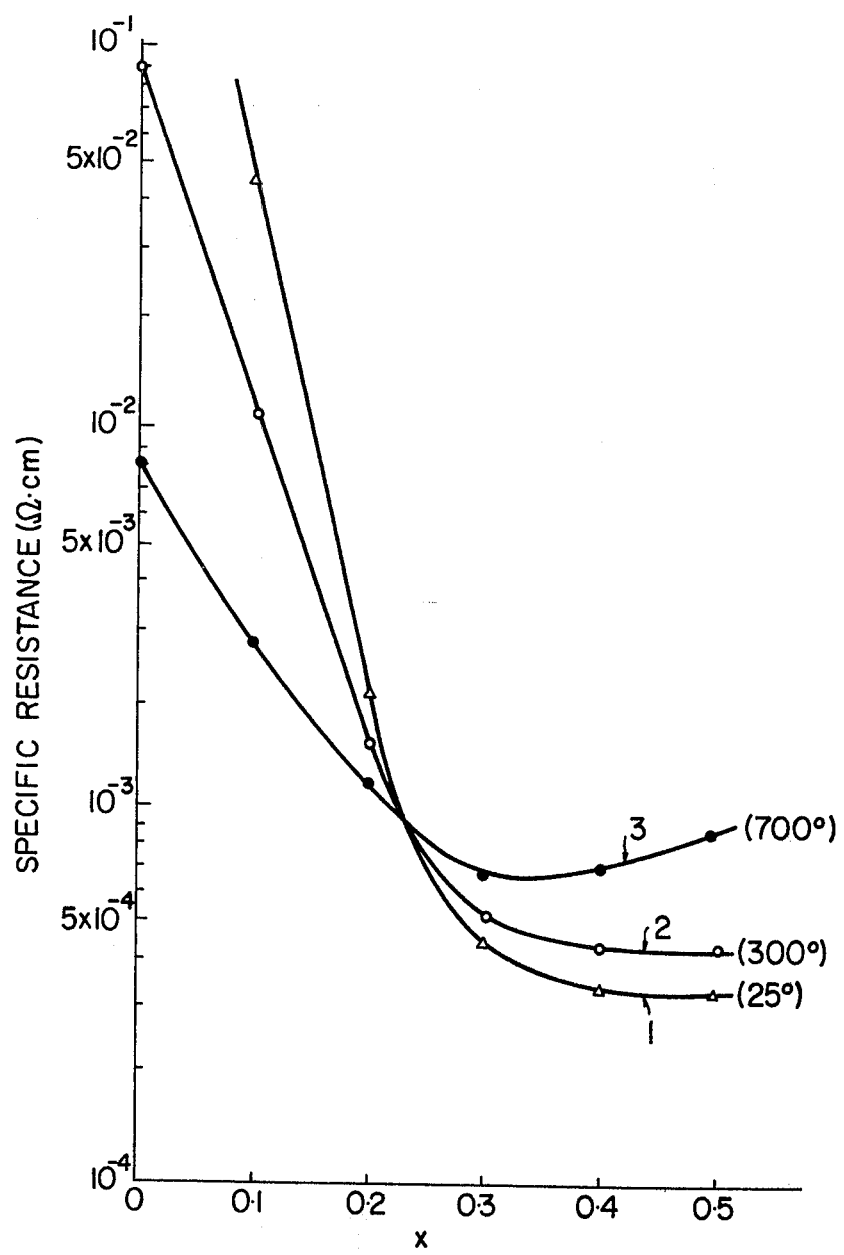
FIG. 1 is the isothermal diagram representing the relationship between the composition ($x$) of the complex metal oxide $Nd_{1-x}Sr_xCoO_3$ and the specific resistance.

It was already reported that certain complex metal oxides having a perovskite-type crystal structure and represented by the general formula $A_{1-x}A'_xBO_{3-\delta}$ (-hereinafter referred to simply as complex oxide and the number of oxygen atoms in the formula is expressed as 3, δ being omitted from the expression unless specially needed) show a favorable electric conductivity. The present inventors have now found that the specific resistance of the complex oxide is correlated with the concentration of a reducing gas or the concentration of oxygen in an atmosphere, under which the complex oxide is placed, and thus accomplished the present invention.

For synthesizing the above-said complex oxide, there are available various methods. For instance, in synthesizing from oxides, predetermined amounts of the component oxides are weighed out, ground finely, and mixed thoroughly. A sample is obtained by sintering the oxide mixture at between 1,000° to 1,400° C. for 2 to 24 hours. During the sintering, the oxygen partial pressure is controlled in the following manner. According to the magnitude of the tolerance factor for perovskite structure, either a reducing or an oxidizing atmosphere is used. An oxygen partial pressure in the range of $10^{-20}$ to 1 atmosphere is suitably selected. If the selection of atmosphere is improper, the result is not a perovskite structure but an oxide or an oxide mixture of different structure. After sintering the sample is quenched, if necessary, in liquid nitrogen or in ice water at 0° C.

In synthesizing from carbonates, nitrates, oxalates, or acetates, predetermined amounts of these salts are weighed out and treated at 500° to 1,200° C. in a manner similar to that in the case of oxides. When there is a large difference between the decomposition temperatures of the salts and the temperature of formation of the perovskite structure, decomposition should be brought to completion by supplying air or oxygen during the decomposition. As compared with the method in which oxides are used as the starting material, the present method is characterized by capable of synthesizing the perovskite-type oxide at a lower temperature. The method has further advantages over the oxide in that since the components can be mixed by wet process, it is possible to obtain more uniform and more finely powdered complex oxide.

A method which makes use of an alkali metal carbonate as a flux is useful when it is desired to obtain a perovskite-type oxide which cannot be obtained by either of the above two methods. As the flux, it is preferred to use carbonates of alkali metals such as lithium, potassium, and sodium, or mixtures of these carbonates. For example, single-phase $LaNiO_3$ cannot be obtained even under a controlled atmosphere. On the contrary, when a predetermined amount of a mixture of oxide components or a mixture of decomposition products of salts is thoroughly mixed with sodium carbonate in a ratio of 1 : 1 by weight and kept at a temperature above the melting point of sodium carbonate, i.e. 851° C., for example, at 900° C. for 3 hours, the product contains $LaNiO_3$ as the main constituent. The said product is kept at the said temperature for 10 hours or more and then freed from the carbonate to obtain single-phase $LaNiO_3$.

Figure 16:
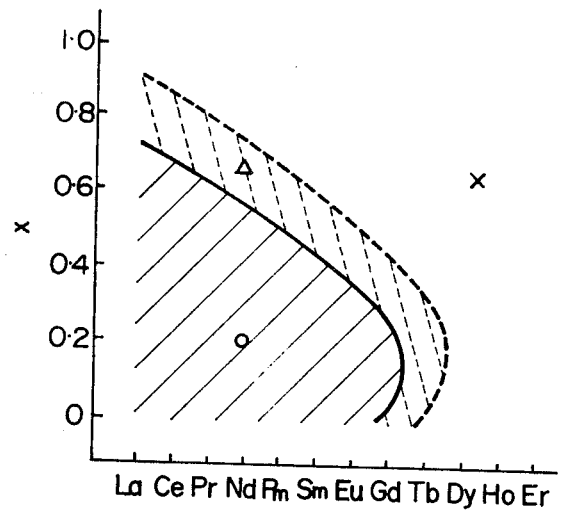
FIGS. 16, 17, and 18 are diagramatic representations of the range of $x$, wherein the perovskite-type crystal structure exists, in the complex oxides $A_{1-x}Ca_xCoO_3$, $A_{1-x}Sr_xCoO_3$, and $A_{1-x}Ba_xCoO_3$, respectively.
Figure 17:
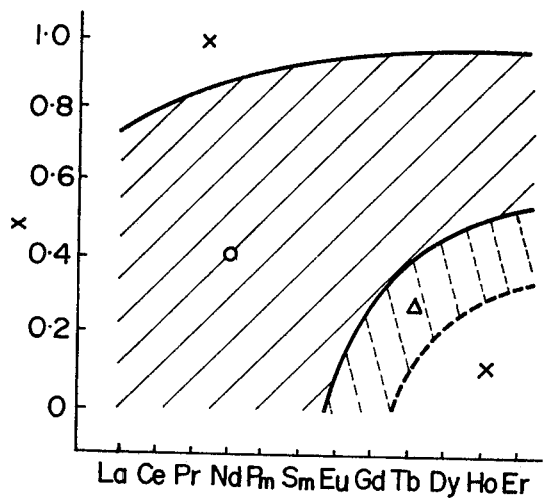
Figure 18:
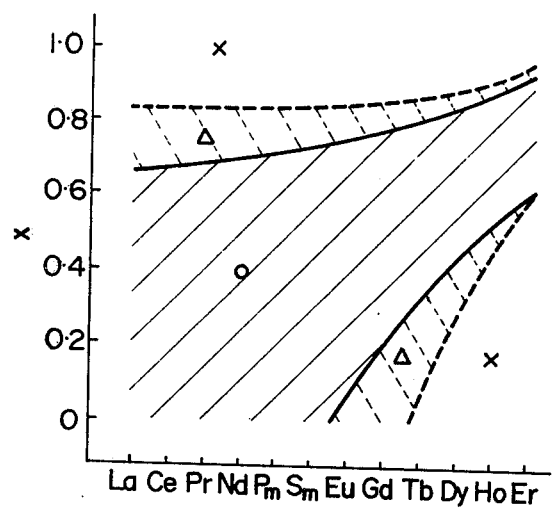

On the other hand, the complex oxide having a perovskite-type crystal structure is not always obtained throughout the entire range of composition covered by the aforesaid general formula. For instance, when cobalt is selected as the element B in the general formula, calcium, strontium, or barium as the element A', and various rare earth elements as the element A, the range of $x$ wherein a perovskite-type crystal structure is formed is as shown in FIGS. 16, 17, and 18. These Figures, however, represent the cases where acetates used as starting materials are mixed and sintered in air at 1,000° C. for 7 hours. If the sintering is conducted under an atmosphere which has been controlled for the oxygen partial pressure as mentioned before, the range of $x$ wherein a perovskite-type crystal structure is formed can be made broader.

FIG. 16 relates to $A_{1-x}Ca_xCoO_3$, FIG. 17 to $A_{1-x}Sr_xCoO_3$, and FIG. 18 to $A_{1-x}Ba_xCoO_3$, respectively. The region hatched with solid oblique lines and marked with O represents region of the perovskite-type crystal structure, the region hatched with dotted oblique lines and marked with Δ represents the region where the perovskite-type crystal structure is mixed with other oxide phases to form two or more phases, and the region marked with $x$ represents the region where no perovskite structure is formed.

Strontium is desirable to be used as the element A', because a perovskite-type crystal structure is formed over a broad range of $x$.

The above-said complex oxides are used in the form of shaped piece or film as a sensing element.

When it is intended to obtain a sensor element in the form of plate, rod, or disc, the complex oxide is shaped into any desired form and then sintered at 800° to 1,100° C. for 0.5 to several hours. When it is intended to obtain a coating in the form of film on an alumina plate, a silica glass, or other suitable base-plates, the complex oxide is mixed with a PVA (polyvinyl alcohol) solution, or a methylcellulose solution to form a slurry which is coated on a base plate, and then sintered in a manner similar to that mentioned above, to form a sensing element. Further, the complex oxide can be supported on a porous carrier or mixed with an inert powder, and then sintered. The porosity of the element thus prepared is generally in the range of 60 to 70 %. It is needless to say that in any case the element show better performance characteristics when used in the form having greater specific surface area.

It was already mentioned in the foregoing that quite different from an ordinary oxide, the perovskite-type complex oxide has an extremely high electric conductivity even at room temperature. In FIG. 1 is shown, as an example, the results of measurement of specific resistance conducted on a specimen, about 35 mm long, about 10 mm wide, and about 3 mm thick, prepared by sintering a complex oxide of the formula $Nd_{1-x}Sr_xCoO_3$. In the Figure, the curves 1, 2, and 3 are plots of the data obtained in air at 25°, 300°, and 700° C., respectively. As is clear from the Figure, it is seen that the specific resistance decreases with the increase in $x$. As is seen also from this example, it has been known that the specific resistance decreases as the number of oxide components increases from binary oxide to ternary and more multiplicated system. Thus, those complex oxides are preferable for use which are of the general formula in which $x$ is within the range $0 < x < 1$.

The data on specific resistance mentioned hereinafter were obtained from the measurement conducted on the test specimen having nearly the same form as that mentioned above.

It is also known that in a perovskite-type oxide represented by the formula $A_{1-x}A'_xBO_{3-\delta}$, the nonstoichiometric parameter δ varies easily according to the oxygen partial pressure during formation of the oxide and to the subsequent heat history of the oxide. Consequently, the specific resistance also varies to some exent according to said conditions.

On the other hand, when air containing minute amounts of a reducing gas, such as, for example, the air containing about 0.2 mg/liter of ethanol is allowed to contact with the aforesaid element while being heated at 100° to 500° C., oxygen ions are liberated from the complex metal compound to oxidize ethanol, and the specific resistance of the shaped piece increases with the liberation of oxygen ions. The variation rate of resistance amounts to the order of several ten percent for an ethanol concentration of about 0.2 mg/liter, a concentration usually found, for example, in the breath of an individual who took an alcoholic beverage. The response of the resistance change is also rapid. The temperature coefficient of resistance of the perovskite-type oxide is, in most of the cases, about 0.2%/° C. or smaller at room temperature to 800° C., and the signal-to-noise ratio (S/N ratio) is also so favorable as may be left out of consideration in practical applications. Further, another important feature of the present material is recovery of resistance to the initial resistance due to re-entry of oxygen from air into the perovskite crystal when the material is left in the air after contacting with ethanol. Thus, the material may be utilized as an ethanol sensor with favorable stability and reproducibility.

Although the foregoing explanation is given by reference to ethanol as an example, circumstances are the same with other reducing gases.

The catalytic action of the above-said complex oxide is explained below with reference to ethanol as an example. The oxidation of ethanol seems to take place by the following reactions:

$$C_2H_5OH + 6\ Cat.(O^*) \longrightarrow 2\ CO_2 + 3H_2O + 6\ Cat.(V) \quad (1)$$
$$+ 6\ Cat.(V) + 3\ O_2 \longrightarrow 6\ Cat.(O^*) \quad (2)$$
$$\overline{C_2H_5OH + 3\ O_2 \longrightarrow 2\ CO_2 + 3\ H_2O} \quad (3)$$

where

Cat. O*): oxygen in the complex oxide crystal,
Cat. (V): oxygen vacancy in the complex oxide crystal.

If the rates of reactions (1) and (2) are denoted by $k_1$ and $k_2$, respectively, then the following equations should hold:

$$k_1 = A_1 \exp(-\Delta E_1/k_B\tau) \quad (4)$$

$$k_2 = A_2 \exp(-\Delta E_2/k_B\tau) \quad (5)$$

where
$A_1, A_2$: constant
$\Delta E_1, \Delta E_2$: activation energy of the reaction
$k_B$: Boltzmann's constant
$\tau$: Absolute temperature
The relation between the activation energy of reaction, $\Delta E_1$ and $\Delta E_2$, is estimated as $$\Delta E_1 < \Delta E_2 \quad (6)$$

Figure 2:
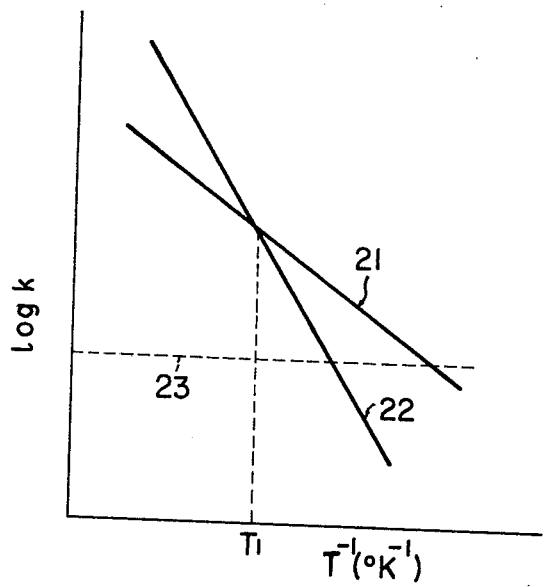
FIG. 2 is the schematic diagram illustrating the change in the rate of reaction with the change in temperature in the case of catalytic oxidation of ethanol with the perovskite-type complex oxide.

The relation between $\tau^{-1}$ and $\log k$ is shown schematically in FIG. 2. The straight lines 21 and 22 show the temperature dependency of the rate of reactions (1) and (2), respectively. The dotted straight line 23 show the lower limit above which the reactions substantially takes place.

With special regard to the variation in oxygen content of a sensor element comprising the complex oxide during oxidation of ethanol, the following scheme may be presumed. Under the given conditions of the temperature $\tau$ and the oxygen partial pressure $P_{O_2}$ at the temperature $\tau$, the complex oxide assumes a $\delta$ value ($\delta_o$) so that the composition may be

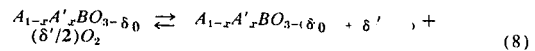

corresponding to the existing equilibrium. When ethanol is supplied, the complex oxide acts as a catalyst and the composition shifts according to the following formula:

$$A_{1-x}A'_xBO_{3-\delta_0} \rightleftarrows A_{1-x}A'_xBO_{3-(\delta_0 + \delta')} + (\delta'/2)O_2 \quad (8)$$

As compared with the composition in the absence of ethanol, the composition of the complex oxide catalyst assumes a greater $\delta$ value, i.e. $\delta_o + \delta'$, which is determined by the ratio between each rate of the reactions (1) and (2). The temperature of the sensor element seems also to be increased to some degree due to enthalpy of the oxidation reaction of ethanol.

Figure 3:
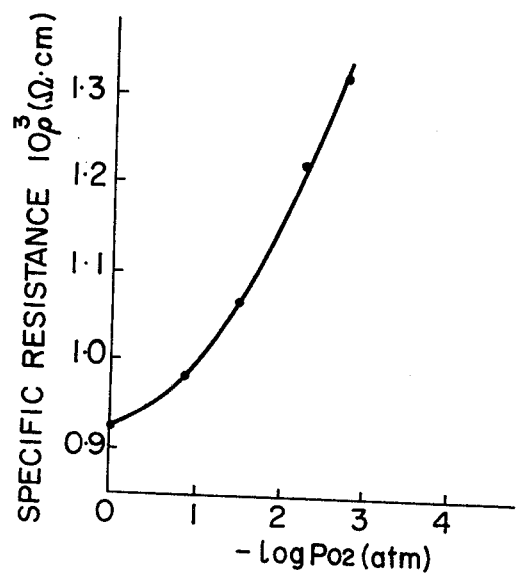
FIG. 3 is a diagram representing the relationship between the equilibrium oxygen partial pressure of the complex oxide $Sm_{0.6}Sr_{0.4}CoO_3$ and the specific resistance.

In FIG. 3 is shown the change in specific resistance with the change in oxygen partial pressure in the atmosphere with respect to $Sm_{0.6}Sr_{0.4}CoO_{3-\delta}$. As is clear from FIG. 3, it is seen that in a complex oxide the decrease in oxygen partial pressure in the atmosphere results in the increase in specific resistance.

As is shown by the formula (8), the complex oxide assumes a larger $\delta$ value in the presence of ethanol than in the absence thereof and it is clear from FIG. 3 that the difference in $\delta$ results in the change in resistance of the test specimen. Thus, these phenomena clearly suggest that the complex oxides be useful as the sensing elements for reducing gases, of which ethanol is a representative.

Now, as mentioned before, the straight lines 21 and 22 in FIG. 2 represent temperature dependency of rate of reactions according to the equations (4) and (5), respectively, which correspond to the reactions (1) and (2), respectively. In the Figure, the temperature range can be divided into three zones according to the relative magnitude of reaction rates $k_1$ and $k_2$ in the following manner:

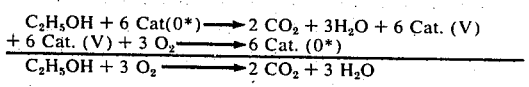

where $\tau_1$ is the temperature at which $k_1$ becomes equal to $k_2$. At $\tau = \tau_1$, equilibrium is attained when $\delta$ becomes ($\delta_o + \delta_1$), a value shifted from $\delta_o$ by $\delta_1$, said $\delta_o$ being the $\delta$ value in the equilibrium composition in the absence of ethanol. Similarly, $\delta$ in the equilibrium compositions in other temperature zones are as follows:

$$\begin{aligned}
\tau < \tau_1 & \quad \delta > \delta_o(\tau_1, P_{o_2}) + \delta_1(\tau, C_{E+OH}) \\
\tau = \tau_1 & \quad \delta = \delta_o(\tau_1, P_{o_2}) + \delta_1(\tau, C_{E+OH}) \\
\tau > \tau_1 & \quad \delta < \delta_o(\tau_1, P_{o_2}) + \delta_1(\tau, C_{E+OH})
\end{aligned} \quad (10)$$

where $\delta_o(\tau, P_{o_2})$ and $\delta_1(\tau, C_{E+OH})$ represent that $\delta_o$ and $\delta_1$ are functions of temperature and oxygen partial pressure or ethanol concentration. From these formulas it is anticipated that in the presence of an alcohol the nonstoichiometric parameter $\delta$ becomes larger with the decrease in temperature, and accordingly, the change in specific resistance also becomes larger with the decrease in temperature. On the other hand, the dotted straight line 23 in FIG. 2 represents the lower limit of the practically significant rate of reaction. It is understandable that with the decrease in temperature the rate of reaction diminishes rapidly until the reactions (1) and (2) no longer practically take place, and accordingly, relative amount of the effectiveness of the catalyst also decreases, accompanied by the decrease in change of the nonstoichiometric parameter $\delta$. It seems that as the overall result of the above-said two competitive tendencies, the maximum change in specific resistance occurs at a certain temperature. This suggests that there exists an optimum range of operating temperatures for the sensor.

The invention is illustrated below in further detail with reference to Examples.

Example 1

A complex oxide, $Nd_{0.77}Sr_{0.23}CoO_3$, was mixed with a PVA solution to form a slurry and the slurry was coated on an alumina base-plate to cover an area measuring 2 mm wide by 7 mm long. Then, the coated oxide was sintered to obtain an element.

Figure 4:
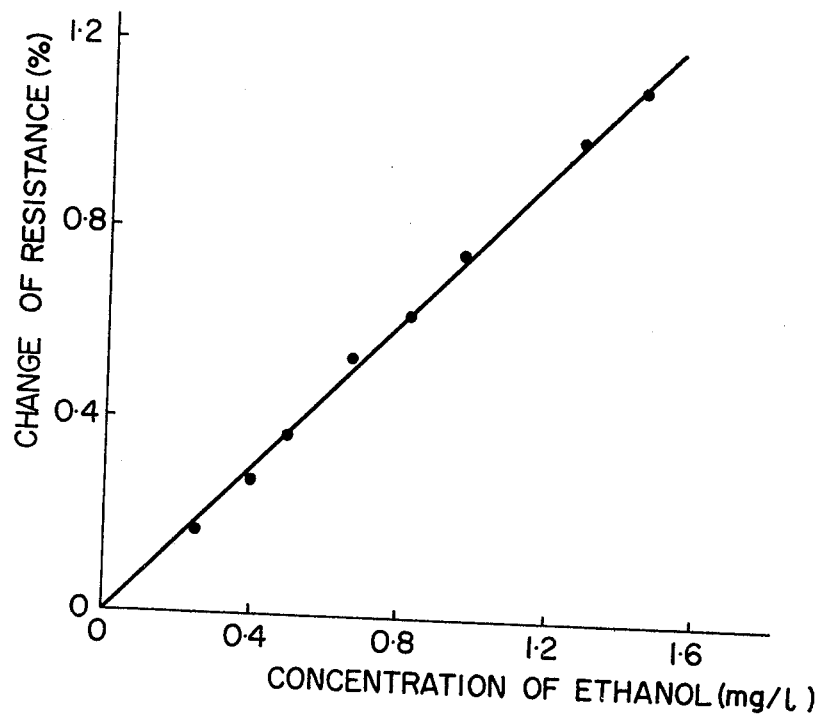
FIG. 4 is a diagram representing the relationship between the ethanol concentration and the change of resistance of an element comprising $Nd_{0.77}Sr_{0.23}CoO_3$.

In FIG. 4 is shown the relationship between the ethanol concentration and the change of resistance of the element placed under an atmosphere containing ethanol. The data were obtained at 390° C. The resistance of the element was 0.16 $\Omega$. It is seen that there exists a sufficiently linear relation between the change of resistance and the ethanol concentration within the range of concentration (0 to 2 mg/liter) usually found in the breath of an individual who has taken an alcoholic beverage. As will be appreciated by those skilled in the art, changes in resistance are measured by apparatus. This apparatus will be referred to in the specification and claims as means for measuring the change in resistance of the material being referred to.

EXAMPLE 2

Figure 5:
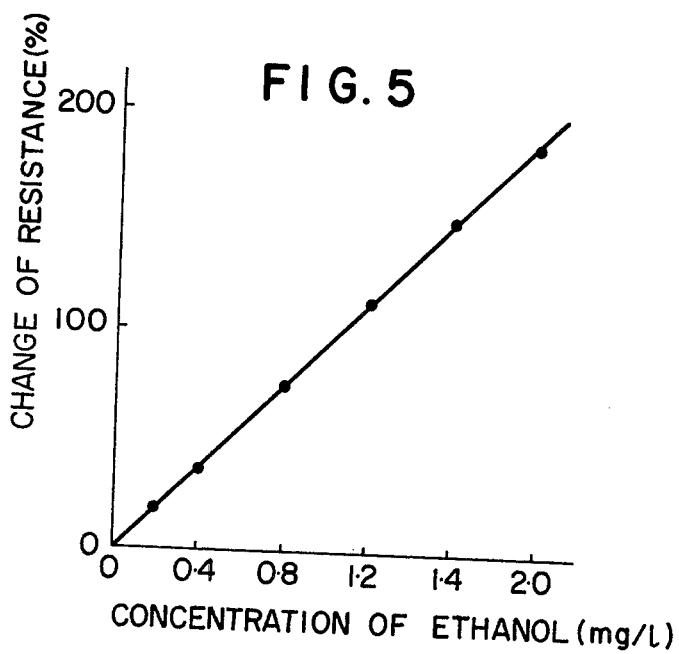
FIG. 5 is a diagram representing the relationship between the ethanol concentration and the change of resistance of an element comprising $LaNiO_3$.
Figure 6:
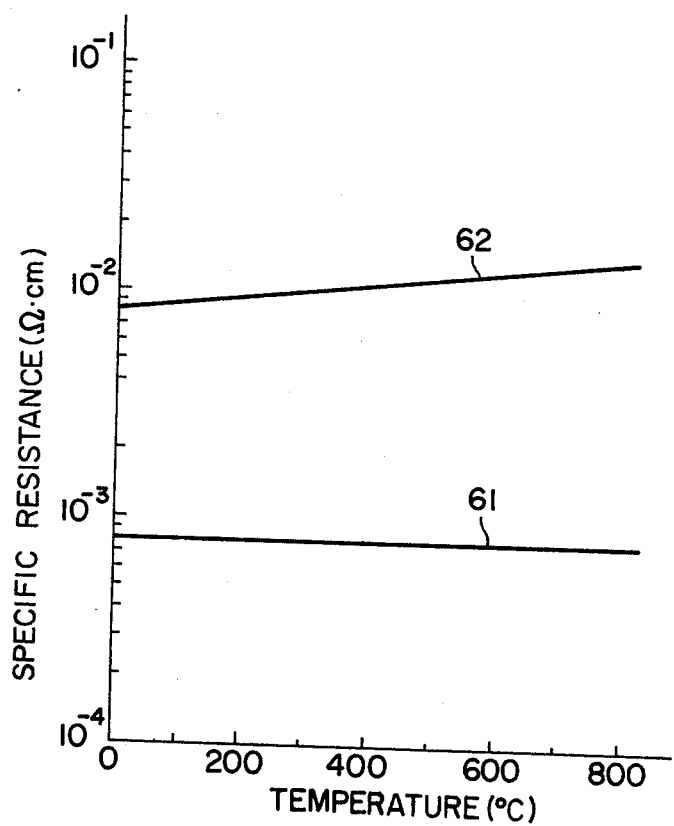
FIG. 6 is the diagram representing the change in specific resistance of elements comprising $Nd_{0.77}Sr_{0.23}CoO_3$ and $LaNiO_3$, respectively, with the change in temperature.

An element similar to that in Example 1 was prepared by use of $LaNiO_3$. In FIG. 5 is shown the behavior of the element in detecting ethanol at 250° C. From the Figure it is seen that similarly to the case in Example 1, the relationship between the concentration and the variation rate of resistance of the element is also sufficiently linear. By comparison of FIG. 4 with FIG. 5, it may be said that $Nd_{0.77}Sr_{0.23}CoO_3$ shows a smaller change of resistance than $LaNiO_3$. Generally speaking, nickel often shows a large change. However, as shown in FIG. 6, $Nd_{0.77}Sr_{0.23}CoO_3$ (curve 61 in FIG. 6) is characterized to be of smaller temperature coefficient of resistance than that of $LaNiO_3$ (curve 62 in FIG. 6), and may be effectively employed in the case where a sensing element of small temperature coefficient of resistance is required.

Figure 7:
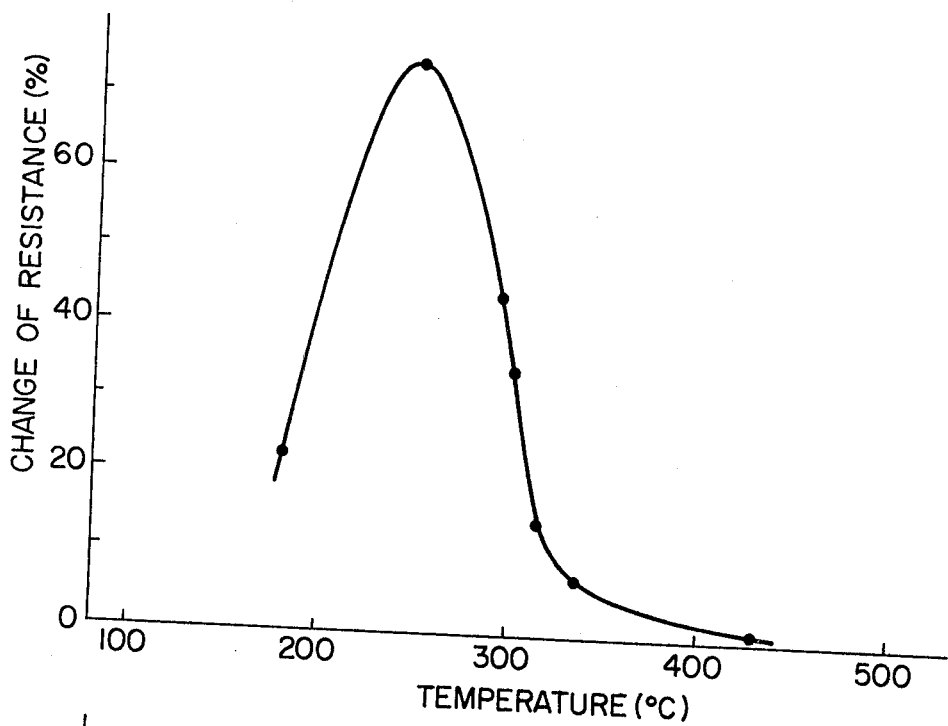
FIG. 7 is a diagram representing temperature dependency of the change of resistance of an element comprising $LaNiO_3$.

In FIG. 7 is shown temperature dependency of the change of resistance of the element in the presence of 0.8 mg/liter of ethanol. As fully discussed hereinbefore, on examination of the catalytic reaction of an alcohol resolved into two steps, a suggestion is offered for the possible existence of an optimum temperature for the change of resistance. It is seen in FIG. 7 that the present element has such an optimum temperature at 250° C. or thereabout.

COMPARATIVE EXAMPLE 1

Figure 8:
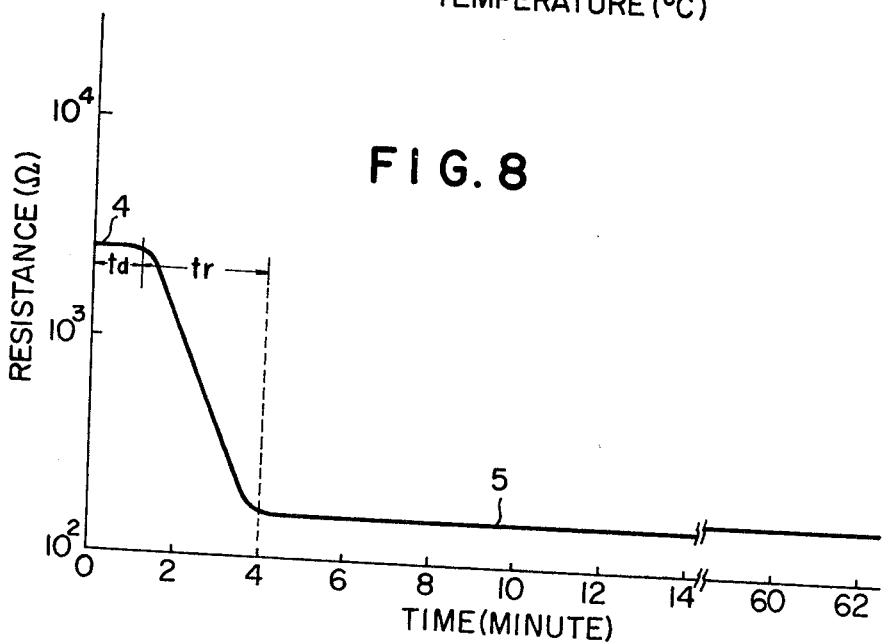
FIG. 8 is a diagram representing the response characteristics of n-type tin oxide conventionally used as an ethanol-sensing element.

In FIG. 8 are shown the results obtained by using n-type tin oxide ($SnO_2$) which has been known as an ethanol-sensing element. In the Figure, $t_d$ represents a dead time and $t_r$ a response time. Supply of ethanol was started at the point 4 and discontinued at the point 5. The temperature was 170° C. As is seen from the Figure, with the supply of ethanol the resistance decreases to a figure down about one place. However, the trouble in this case is that as is seen from the Figure, the initial resistance is not restored even in the absence of ethanol. Therefore, the element is entirely unsuitable for the continual-repetitive at a constant temperature.

In Table 1 are shown $t_d$ and $t_r$ observed for tin oxide at various temperatures.

Table 1

| Reaction temperature (°C.) | td (sec.) | tr (sec.) | Initial resistance (k$\Omega$) | Final resistance ($\Omega$) |
|---|---|---|---|---|
| 144 | 50 | 180 | 4.2 | 300 |
| 200 | 5 | 20 | 16 | 120 |
| 260 | 5 | 15 | 12 | <1,000 |
| 340 | 5 | 15 | 110 | 1,300 (Returns to the initial value in 4 min.) |

From the table, it is seen that restoration of initial resistance is resulted when the element is heated at a temperature of about 350° C. or higher. This indicates that in the case of an element comprising a semiconductor such as n-type tin oxide, although the change in its resistance is large due to adsorption of ethanol, restoration of the initial resistance is not possible unless the adsorbate is desorbed because said element lacks catalytic activity for oxidation. Consequently, the element is unsuitable for continued use at lower temperatures, as is the case with the sensing element comprising perovskite-type oxide according to this invention. It was also observed that when used at a temperature above 350° C., the element comprising tin oxide deteriorates severely.

EXAMPLE 3

In a manner similar to that in Example 1, an element was prepared by use of $LaNiO_3$. In Table 2 are shown sensing performance of the element for various gases at 250° C. In the Table, the mark (+) and (−) show occurrence and absence, respectively, of the change in resistance. The number of (+) shows relative magnitude of the change in resistance.

Table 2

| Sample gas | Response of sensor |
|---|---|
| Acetone | +++ |
| Ethanol | +++ |
| Methanol | +++ |
| Petroleum benzine | ++ |
| Toluene | + |
| Benzene | + |
| Ether | +++ |
| Water | − |
| Hydrogen peroxide | − |
| Trichloroethylene | ++ |
| Ammonia | − |
| Carbon monoxide | +++ |

EXAMPLES 4 to 29

Elements similar to that in EXAMPLE 1 were prepared by using various complex oxides. The sensing performance of these elements for ethanol 250° C. are shown in Table 3.

Table 3

| Example No. | Complex oxide | Specific resistance (Ω-cm) | Gas sensing performance |
|---|---|---|---|
| 4 | $YCrO_3$ | $\sim 10^2$ | + |
| 5 | $YFeO_3$ | $\sim 10$ | +++ |
| 6 | $Hf_{0.1}La_{0.8}Sr_{0.1}CoO_3$ | $7 \times 10^{-3}$ | ++ |
| 7 | $La_{0.8}Sr_{0.2}Co_{0.9}Ni_{0.1}O_3$ | $6 \times 10^{-4}$ | ++ |
| 8 | $La_{0.8}Sr_{0.2}Co_{0.8}Ni_{0.1}O_3$ | $1 \times 10^{-3}$ | ++ |
| 9 | $Nd_{0.9}Sr_{0.05}Ba_{0.05}CoO_3$ | $4 \times 10^{-2}$ | ++ |
| 10 | $Nd_{0.8}Sr_{0.1}Ba_{0.1}CoO_3$ | $2.6 \times 10^{-3}$ | +++ |
| 11 | $La_{0.1}Sr_{0.9}MnO_3$ | $\sim 10^2$ | + |
| 12 | $La_{0.2}Sr_{0.8}FeO_3$ | $\sim 10^{-1}$ | ++++ |
| 13 | $Pr_{0.75}Sr_{0.25}MnO_3$ | $\sim 10^{-1}$ | ++ |
| 14 | $Pr_{0.25}Sr_{0.75}FeO_3$ | $\sim 10^0$ | ++++ |
| 15 | $Pr_{0.8}Sr_{0.2}CoO_3$ | $5 \times 10^{-4}$ | +++ |
| 16 | $Pr_{0.5}Sr_{0.5}CoO_3$ | $3.8 \times 10^{-4}$ | ++++ |
| 17 | $Sm_{0.5}Sr_{0.5}FeO_3$ | $2.4 \times 10^{-2}$ | ++++ |
| 18 | $Sm_{0.2}Sr_{0.8}CoO_3$ | $3.4 \times 10^{-4}$ | +++ |
| 19 | $Y_{0.25}Sr_{0.75}MnO_3$ | $\sim 10^1$ | ++ |
| 20 | $SrCo_{0.5}Fe_{0.5}O_3$ | $\sim 10^0$ | ++++ |
| 21 | $Sm_{0.5}Sr_{0.5}Co_{0.8}Fe_{0.2}O_3$ | $1.8 \times 10^{-3}$ | ++++ |
| 22 | $La_{0.995}Sr_{0.005}Ni_{0.8}Fe_{0.2}O_3$ | $5 \times 10^{-3}$ | ++++ |
| 23 | $CaMnO_3$ | $2 \times 10^2$ | ++ |
| 24 | $Nd_{0.5}Sr_{0.5}CoO_3$ | $2.1 \times 10^{-4}$ | +++ |
| 25 | $Gd_{0.5}Sr_{0.5}CoO_3$ | $1.4 \times 10^{-4}$ | ++++ |
| 26 | $Dy_{0.5}Sr_{0.5}CoO_3$ | $3 \times 10^{-2}$ | ++++ |
| 27 | $Er_{0.5}Sr_{0.5}CoO_3$ | $8 \times 10^{-1}$ | +++ |
| 28 | $Yb_{0.5}Sr_{0.5}CoO_3$ | $4 \times 10^0$ | +++ |
| 29 | $Pr_{0.769}Sr_{0.231}MnO_3$ | $\sim 10^1$ | ++ |

EXAMPLE 30

Figure 9:
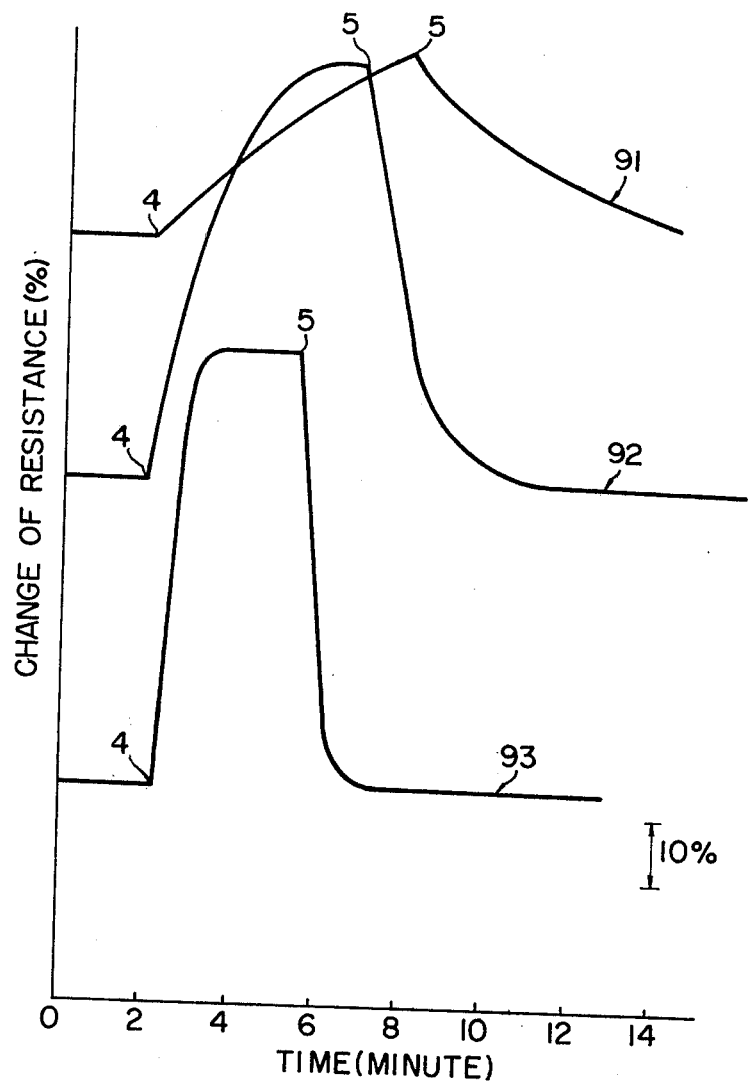
FIG. 9 is a diagram showing response characteristics of the elements comprising $LaNiO_3$.

By using elements in various forms, which comprised $LaNiO_3$, behavior of each element in detecting ethanol was tested to obtain the results as shown in FIG. 9. The curve 91 represents the behavior of a cylindrical element, 5.75 mm in diameter and 6.95 mm in height; the curve 92 that of a cylindrical element, 3.00 mm in diameter and 4.0 mm in height; and the curve 93 that of an element in the form of rectangular film, 2.00 mm in width and 7.00 mm in length, coated on an alumina base-plate. In the Figure, supply of ethanol was started at the point 4 and discontinued at the point 5. The temperature of measurement was 250° C. From FIG. 9 it is seen that a favorable response is obtained from the element in the form which provides a large surface of contact with a gas so that the reaction may take place rapidly.

EXAMPLE 31

Figure 10:
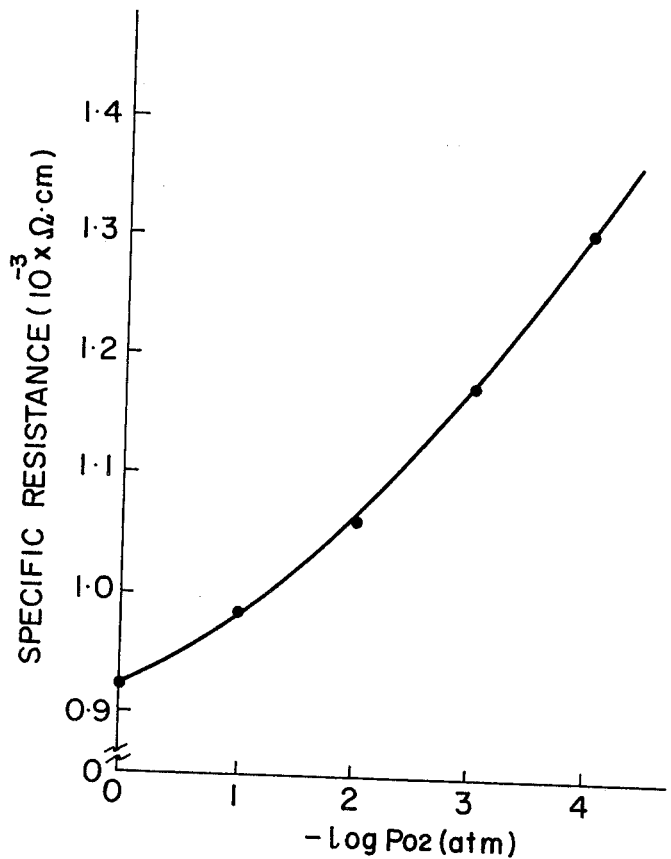
FIG. 10 is a diagram representing the relationship between the oxygen partial pressure and the specific resistance of an element comprising $Sm_{0.4}Sr_{0.6}CoO_3$.

An element similar to that in Example 1 was prepared by use of $Sm_{0.4}Sr_{0.6}CoO_3$. In FIG. 10 is shown the change in specific reistance of the element at 500° C. with the change in oxygen partial pressure. It is seen that the specific resistance of the complex oxide changes in accordance with the change in oxygen partial pressure and that there is a difference amounting to about 20% between the specific resistance in the air and that in an atmosphere containing 1% oxygen.

EXAMPLE 32

Figure 11:
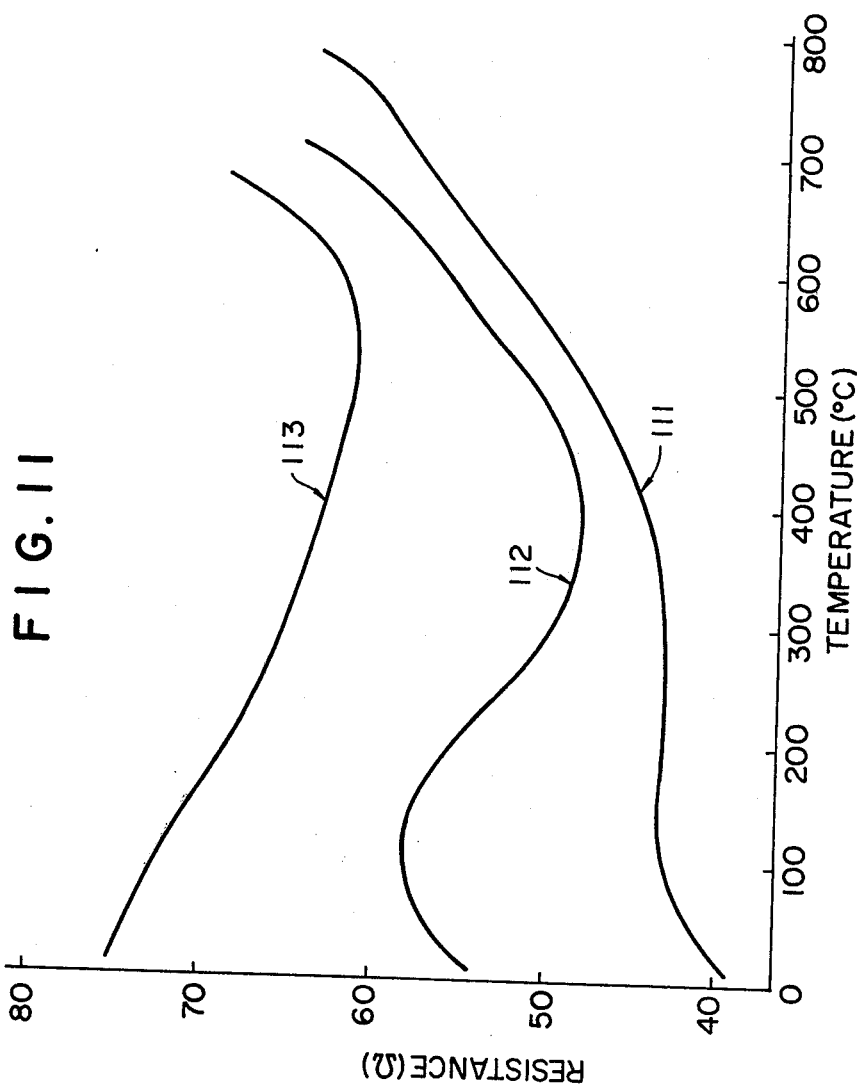
FIG. 11 is the diagram representing the relationship between the resistance of an element comprising $La_{0.993}Sr_{0.007}NiO_3$ and the temperature.

In FIG. 11 are shown temperature dependencies of the resistance of a sensing element comprising $La_{0.993}Sr_{0.007}NiO_3$ under atmospheres containing oxygen in various concentrations. The element used was prepared by coating the complex oxide on an alumina base-plate to a thickness of about $5\mu$ to cover an area of 3 mm width by 12 mm length, an then sintered. In FIG. 11, the curves 111, 112 and 113 show the resistance of the element in oxygen ($P_{o_2} = 1.0$ atm), air ($P_{o_2} = 0.21$ atm), and a gas mixture of 1% $O_2$—$N_2$ ($P_{o_2} = 0.01$ atm), respectively.

When the element B in the general formula is cobalt, a particularly favorable sensitivity is shown by a composition in which $x$ (a factor relating to the proportion of $A'$ which replaced a part of A) is large, whereas when the element B is nickel, a favorable sensitivity is shown regardless of whether $x$ is large or small or even zero. This is presumably because $Ni^{2+}$ is stable as well as $Ni^{+3}$ in the complex oxide.

Figure 12:
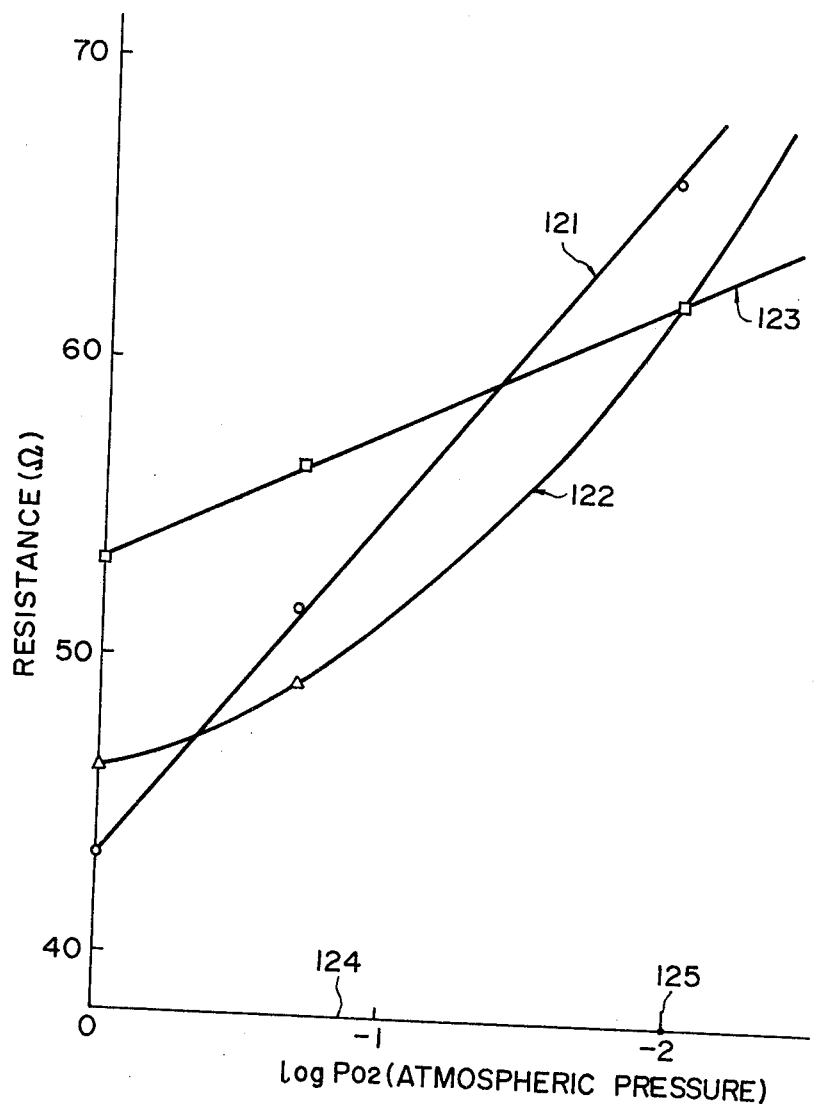
FIG. 12 is the diagram representing the relationship between the resistance of the same element as in FIG. 11 and the oxygen partial pressure.

In FIG. 12 is shown the change in resistance of the element with the change in oxygen partial pressure. The curves, which were plotted on the basis of data shown in FIG. 11, represent dependency of the resistance on oxygen partial pressure. The curves 121, 122, and 123 represent the said dependency at 250°, 450°, and 600° C., respectively. At 250° C. and 600° C. resistance of the element increases in proportion to oxygen partial pressure. At 450° C. the curve representing dependency of the resistance on the oxygen partial pressure is somewhat convexed downward.

The rate of response of this element increases with the rise in temperature.

In Table 4 is shown, as an example, the rate of response of the element when atmosphere is changed from air (corresponding to the point 124 in FIG. 12) to an atmosphere of 1% oxygen (corresponding to the point 125 in FIG. 12).

Table 4

| Temperature (°C.) | Rate of response (min.) Time constant (0 to 1—1/e response time) |
|---|---|
| 250 | > 25 |
| 450 | 3.8 |
| 600 | 1.5 |
| 800 | 0.2 |

The rate of response is improved rapidly with the rise in temperature.

EXAMPLE 33

Figure 13:
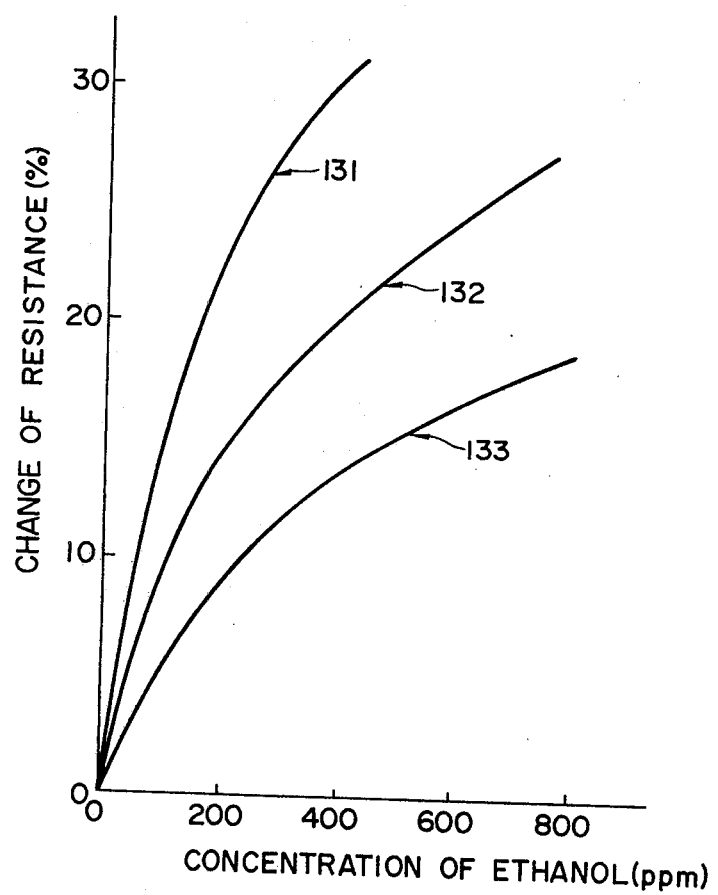
FIG. 13 is the diagram representing the relationship between the ethanol concentration and the change of resistance of an element comprising $Pr_{0.5}Sr_{0.5}CoO_3$.
Figure 14:
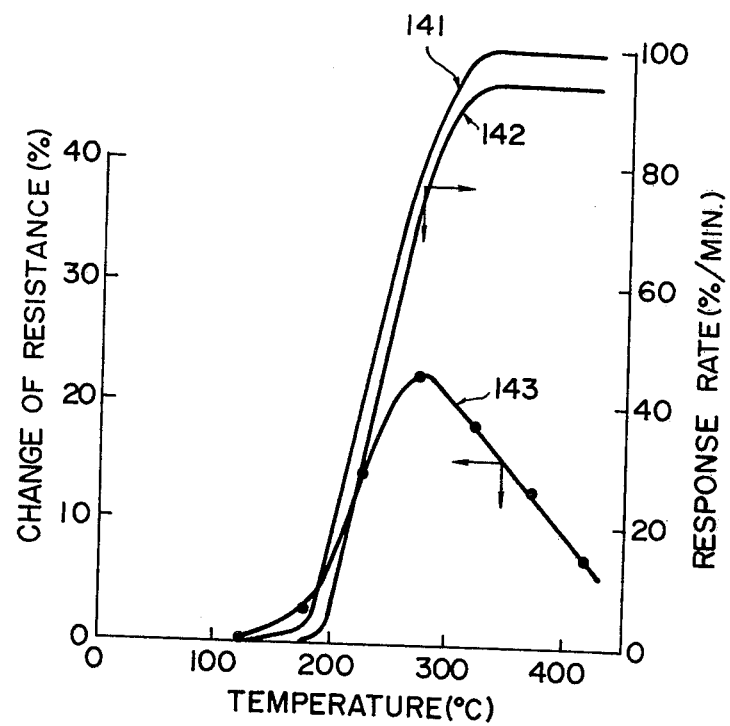
FIG. 14 is the diagram representing the relationship between the temperature and the change of resistance or the response rate of the same element as in FIG. 13.

An element similar to that in Example 1 was prepared by using $Pr_{0.5}Sr_{0.4}CoO_3$. In FIG. 13 is shown the change of resistance of the element relative to the ethanol concentration. The curves 131, 132, and 133 correspond to the temperatures of the element of 325°, 372°, and 417° C., respectively. In FIG. 14 are shown the change of resistance and the response rate under an atmosphere containing 150 ppm ethanol. The curves 141, 142, and 143 represent ascent response rate, descent response rate, and change of resistance, respectively. The change of resistance reaches the maximum at about 280° C. and decreases at higher temperatures. The response rate is expressed in terms of percentage of the change in resistance based on the saturation level, which change took place in a period of one minute after contact with ethanol or after termination of contact with ethanol. It is seen that the response rate rapidly changes in the range of 200° to 300° C., and that an optimum temperature range for the element to operate is from about 320° to 330° C. in consideration of the change of resistance and the response rate. The change of resistance relative to the ethanol concentration at a temperature within the said range is shown by the curve 131 of FIG. 13. It is apparent that the complex oxide shows a most favorable response rate as well as a large change of resistance even at higher ethanol concentrations. In comparison with the element in Example 1, it is seen that complex oxides containing cobalt differ from each other in response performance depending upon the kind of rare earth element and the strontium content.

EXAMPLES 34 to 36

Elements similar to that in Example 1 were prepared by using $Pr_{0.25}Sr_{0.75}FeO_3$, $La_{0.2}Sr_{0.8}FeO_3$, and $Sm_{0.5}Sr_{0.5}FeO_3$, respectively. The change of resistance of these elements against 150 ppm ethanol were as shown in Table 5, Table 6, and FIG. 15, respectively.

Table 5

| Temperature (°C.) | ($Pr_{0.25}Sr_{0.75}FeO_3$) Change of resistance (%) |
|---|---|
| 212 | 62 |
| 273 | 134 |
| 334 | 226 |
| 367 | 250 |
| 398 | 340 |
| 451 | 150 |
| 503 | 32 |

Table 6

| Temperature (°C.) | ($La_{0.2}Sr_{0.8}FeO_3$) Change of resistance (%) |
|---|---|
| 221 | 35 |
| 287 | 168 |
| 370 | 180 |
| 431 | 163 |

Figure 15:
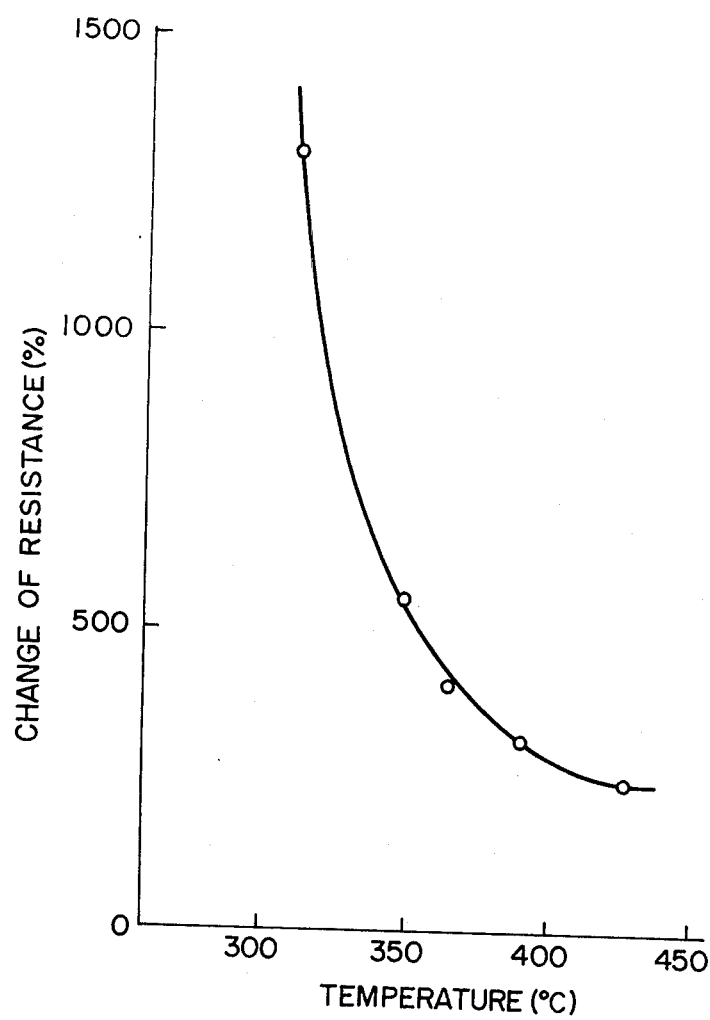
FIG. 15 is a diagram representing the relationship between the temperature and the change of resistance of an element comprising $Sm_{0.5}Sr_{0.5}FeO_3$.

A change of resistance of 1,300% at 310° C. shown in FIG. 15 is one of the highest change in this invention. In this case it was found that with the rise in temperature the change of resistance decreases, whereas the response rate increases.

The above three Examples show that when iron is used as the element B in the general formula, the resulting complex oxide shows a high change of resistance ranging from several hundred to a thousand percent or higher to 150 ppm ethanol. It is to be noted that in these examples selection of the elements A and A' beside B and the amount of doping with A' also greatly affect the change of resistance. While these examples demonstrated the effectiveness of employing iron as the element B, favorable results may also be obtained by joint use of two or more metals such as iron-cobalt, iron-nickel, or iron-nickel-cobalt. In general, incorporation of cobalt in the complex oxide often results in reduced electric resistance, improved reproducibility, and also easier synthesis of the complex oxide.

As stated in the foregoing, the gas-sensor element of this invention is distinguished in sensing performance for an oxidizable gas. Examples of most suitable applications of the element include a sensor for detecting oxidizable gases in the exhaust gas from factorys and shops, an automatic on-off control device for a ventilating fan by means of detecting carbon monoxide in living-environments, a fire and smoke alarm by means of detecting carbon monoxide and smoke, and a sensor for estimating concentration of ethanol in the breath of an individual who has taken an alcoholic beverage.

The gas-sensor element of this invention is also distinguished in determination of the oxygen concentration and is widely applicable to automatic ventilation of air-conditioned dwelling houses and shops by detecting oxygen content of the indoor air, a detection and alarm system for the oxygen-deficient air in mines and building spots, a ventilation system for use in a tunnel by detecting air pollution, a system for detecting air pollution in living-environments under waters, a detection and alarm system for atmospheric pollution in a closed environment, etc.

What is claimed is:

1. In a method for detecting the presence of a gaseous substance in a test gas comprising contacting the test gas with a sensor element whose resistance changes in the presence of said gaseous substance and measuring the resistance of said sensing element while said test gas is in contact therewith, the improvement wherein said gaseous substance is oxygen or a reducing gas and further wherein said sensing element comprises a complex metal oxide having a perovskite-type crystal structure and represented by the general formula $A_{1-x}A'_xBO_{3-\delta}$, wherein A is at least one element selected from the group consisting of rare earth elements of the atomic numbers from 57 to 71, yttrium, and hafnium, A' is at least one alkaline earth metal, B is at least one element selected from the group consisting of transition metals of the atomic numbers from 21 to 30, O is oxygen, $x$ is in the range of $0 \leq x \leq 1$, and $\delta$ is a nonstoichiometric parameter.

2. A method according to claim 1, wherein $x$ in the general formula $A_{1-x}A'_xBO_{3-\delta}$ is in the range of $0 < x < 1$.

3. A method according to claim 1, wherein the complex metal oxide represented by the general formula $A_{1-x}A'_xBO_{3-\delta}$ contains at least cobalt as B.

4. A method according to claim 1, wherein the complex metal oxide represented by the general formula $A_{1-x}A'_xBO_{3-\delta}$ contains at least iron as B.

5. A method according to claim 1, wherein the complex metal oxide represented by the general formula $A_{1-x}A'_xBO_{3-\delta}$ contains at least nickel as B.

6. A method according to claim 1, wherein the complex metal oxide represented by the general formula $A_{1-x}A'_xBO_{3-\delta}$ contains at least strontium as A'.

7. A method according to claim 3, wherein the complex metal oxide represented by the general formula $A_{1-x}A'_xBO_{3-\delta}$ contains at least strontium as A'.

8. A method according to claim 4, wherein the complex metal oxide represented by the general formula $A_{1-x}A'_xBO_{3-\delta}$ contains at least strontium as A'.

9. A method according to claim 5, wherein the complex metal oxide represented by the general formula $A_{1-x}A'_xBO_{3-\delta}$ contains at least strontium as A'.

10. A method according to claim 1, wherein the reducing gas or the gas-containing oxygen is allowed to contact said sensing element at a temperature of about 100°–500° C.

11. A method according to claim 1, wherein detection of the reducing gas or oxygen is carried out by measuring the change in specific resistance of the complex metal oxide.

12. A method according to claim 11, wherein x in the general formula $A_{1-x}A'_xBO_{3-\delta}$ is in the range of $0 < x < 1$.

13. A method according to claim 11, wherein the complex metal oxide represented by the general formula $A_{1-x}A'_xBO_{3-\delta}$ contains at least cobalt as B.

14. A method according to claim 11, wherein the complex metal oxide represented by the general formula $A_{1-x}A'_xBO_{3-\delta}$ contains at least iron as B.

15. A method according to claim 11, wherein the complex metal oxide represented by the general formula $A_{1-x}A'_xBO_{3-\delta}$ contains at least nickel as B.

16. A method according to claim 11, wherein the complex metal oxide represented by the general formula $A_{1-x}A'_xBO_{3-\delta}$ contains at least strontium as A'.

17. A method according to claim 11, wherein the reducing gas or the gas-containing oxygen is allowed to contact said sensing element at a temperature of about 100°–500° C.

18. A method according to claim 1, wherein detection of the reducing gas is carried out by measuring the change in specific resistance of the complex metal oxide when the metal oxide oxidizes or decomposes the reducing gas contacting the metal oxide by catalytic action of the complex metal oxide.

19. A method according to claim 18, wherein $x$ in the general formula $A_{1-x}A'_xBO_{3-\delta}$ is in the range of $0 < 0x < 1$.

20. A method according to claim 18, wherein the complex metal oxide represented by the general formula $A_{1-x}A'_xBO_{3-\delta}$ contains at least cobalt as B.

21. A method according to claim 18, wherein the complex metal oxide represented by the general formula $A_{1-x}A'_xBO_{3-\delta}$ contains at least iron as B.

22. A method according to claim 18, wherein the complex metal oxide represented by the general formula $A_{1-x}A'_xBO_{3-\delta}$ contains at least nickel as B.

23. A method according to claim 18, wherein the complex metal oxide represented by the general formula $A_{1-x}A'_xBO_{3-\delta}$ contains at least strontium as A'.

24. A method according to claim 18, wherein the reducing gas or the gas-containing oxygen is allowed to contact said sensing element at a temperature of about 100°–500° C.

25. In a gas-sensor for detecting the presence of a gaseous substance in a test gas, said gas-sensor including sensing element whose resistance changes in the presence of said gaseous substance, said sensing element having a surface capable of coming into contact with said test gas and indicating means for indicating the presence of said gaseous substance in said test gas in response to a change in resistance of said sensing element, the improvement wherein said sensing element is formed from a complex metal oxide having a perovskite-type crystal structure and represented by the general formula $A_{1-x}A'_xBO_{3-\delta}$, wherein A is at least one element selected from the group consisting of rare earth elements of the atomic numbers from 57 to 71, yttrium, and hafnium, and A' is at least one alkaline earth metal, B is at least one element selected from the group consisting of transition metals of the atomic numbers from 21 to 30, O is oxygen, $x$ is in the range of $0 \leq x \leq 1$, and $\delta$ is a nonstoichiometric parameter.

26. A gas-sensor according to claim 25, wherein said sensing element is in the form of a plate, rod or disc.

27. The gas-sensor of claim 25, wherein said complex metal oxide is a coating on a substrate.

28. The gas-sensor of claim 25, further comprising means for keeping the temperature of said complex metal oxide constant.

29. A gas-sensor according to claim 25, where $x$ in the general formula $A_{1-x}A'_xBO_{3-\delta}$ is in the range of $0 < x < 1$.

30. A gas-sensor according to claim 25, wherein the complex metal oxide represented by the general formula $A_{1-x}A'_xBO_{3-\delta}$ contains at least cobalt as B.

31. A gas-sensor according to claim 25, wherein the complex metal oxide represented by the general formula $A_{1-x}A'_xBO_{3-\delta}$ contains at least iron as B.

32. A gas-sensor according to claim 25, wherein the complex metal oxide represented by the general formula $A_{1-x}A'_xBO_{3-\delta}$ contains at least nickel as B.

33. A gas-sensor according to claim 25, wherein the complex metal oxide represented by the general formula $A_{1-x}A'_xBO_{3-\delta}$ contains at least strontium as A'.

34. A gas-sensor according to claim 30, wherein the complex metal oxide represented by the general formula $A_{1-x}A'_xBO_{3-\delta}$ contains at least strontium as A'.

35. A gas-sensor according to claim 31, wherein the complex metal oxide represented by the general formula $A_{1-x}A'_xBO_{3-\delta}$ contains at least strontium as A'.

36. A gas-sensor according to claim 32, wherein the complex metal oxide represented by the general formula $A_{1-x}A'_xBO_{3-\delta}$ contains at least strontium as A'.

* * * * *